United States Patent [19]

Forte et al.

[11] Patent Number: 4,695,282

[45] Date of Patent: Sep. 22, 1987

[54] ACETABULAR CUP ASSEMBLY WITH SELECTIVE BEARING FACE ORIENTATION

[75] Inventors: Mark R. Forte, Pine Brook; Alex Khowaylo, Allendale; Ewald Schloesser, Wayne, all of N.J.

[73] Assignee: Osteonics Corp., Allendale, N.J.

[21] Appl. No.: 821,772

[22] Filed: Jan. 23, 1986

[51] Int. Cl.⁴ .............................................. A61F 2/34
[52] U.S. Cl. ...................................................... 623/22
[58] Field of Search ....................... 623/16, 18, 20, 21, 623/22, 23

[56] References Cited

U.S. PATENT DOCUMENTS

Re. 28,895  7/1976  Noiles .................................. 623/22

FOREIGN PATENT DOCUMENTS 0065482  11/1982  European Pat. Off. ............. 623/22
2261743   9/1975  France ................................. 623/22

Primary Examiner—Richard J. Apley
Assistant Examiner—David J. Isabella
Attorney, Agent, or Firm—Samuelson & Jacob

[57] ABSTRACT

An acetabular cup assembly includes a metal shell component and a plastic bearing insert capable of assembly interoperatively, the metal shell component first being secured in position within an acetabulum and then the plastic bearing insert being receivable within the shell component, first at a preliminary axial position for ascertainment of the circumferential position of the bearing insert and the orientation of the bearing face of the bearing insert relative to the shell component and then at a fully-seated axial position wherein the bearing insert is permanently captured in the shell component, the bearing insert being readily withdrawn from the preliminary axial position for circumferential repositioning to attain appropriate orientation of the bearing face prior to capturing the bearing insert within the shell component.

16 Claims, 9 Drawing Figures

ACETABULAR CUP ASSEMBLY WITH SELECTIVE BEARING FACE ORIENTATION

The present invention relates generally to hip joint prostheses and pertains, more specifically, to an acetabular cup assembly capable of being implanted in stages so as to enable preliminary ascertainment and adjustment of the position of portions of the assembly prior to commitment to a completed implant position.

The use of prosthetic implant devices in the human body for replacing defective, damaged or diseased anatomical joints of the body has become quite well known. One of the more common forms of implant devices is the hip joint prosthesis which provides an interconnection between the femur and the acetabular socket of the pelvis. Conventional prosthetic hip joints usually include an artificial femoral component having a spherical head member which is received within a complementary spherical socket provided by an acetabular cup assembly.

One frequently used form of acetabular cup assembly has a metal shell component, which is secured to the acetabulum, and a bearing insert component, usually constructed of plastic, secured within the metal shell component to complete the cup assembly. It has been suggested that the bearing insert component be assembled with the shell component interoperatively; that is, the shell component is seated permanently within the acetabulum and then the bearing insert component is inserted into the shell component by the surgeon, thereby providing the surgeon with an opportunity, during implant, to assess the cup assembly position and hip joint function using provisional trials and enabling minor adjustments prior to commitment to a final implant position. Thus, the bearing insert component is provided with a bearing face which is angled slightly relative to the lower face of the shell component so that by rotation of the bearing insert component relative to the shell component the orientation and version of the bearing face can be adjusted after seating of the shell component and prior to permanent assembly of the bearing insert component with the shell component.

It is an object of the present invention to provide an acetabular cup assembly capable of being implanted in stages so as to enable preliminary assessment and adjustment of position during implant and prior to commitment to a completed implant position, with greater ease and increased integrity in the completed implant.

Another object of the invention is to provide an acetabular cup assembly of the type described and which enables interoperative assembly with levels of force compatible with the surgical environment.

Still another object of the invention is to provide an acetabular cup assembly of the type described and which enables a high degree of retention so as to preclude inadvertent disassembly by forces usually encountered during service.

Yet another object of the invention is to provide an acetabular cup assembly of the type described and which includes a radiographic marker incorporated into the locking mechanism which secures the bearing insert component with the shell component in the completed assembly.

A further object of the invention is to provide an acetabular cup assembly of the type described and which enables greater flexibility and control of bearing face position and orientation in the completed assembly.

A still further object of the invention is to provide an acetabular cup assembly of the type described and which includes a minimum number of component parts of relatively simple construction for economy of manufacture and use and uniform high quality.

The above objects, as well as still further objects and advantages, are attained by the present invention, which may be described briefly as an acetabular cup assembly capable of being implanted in stages so as to enable preliminary ascertainment and adjustment of position during implant and prior to commitment to a completed implanted position, the acetabular cup assembly comprising: a shell component having an outer surface for enabling permanent implant of the shell component at an implanted position, an upper top, a lower opening and an inner cavity extending into the shell component upwardly from the lower opening; a bearing insert for placement within the cavity of the shell component by movement of the bearing insert in an axial direction into the cavity, the bearing insert being initially movable into a preliminary axial position within the shell component and subsequently movable axially upwardly beyond the preliminary axial position into a fully-seated axial position within the shell component, the bearing insert having a bearing face extending transverse to said axial direction; an alignment and securing arrangement for aligning and securing the bearing insert within the shell component, the alignment and securing arrangement including first alignment and securing means carried by the shell component and second alignment and securing means carried by the bearing insert, the first and second alignment and securing means being generally complementary to one another for engagement when the bearing insert is in either of the preliminary and fully-seated axial positions; the alignment and securing means including alignment and securing elements, the number and circumferential location of the alignment and securing elements being such that the bearing insert may be placed within the cavity in any selected one of a plurality of circumferential positions relative to the shell component for selective orientation of the bearing face relative to the shell component; the alignment and securing elements including preliminary alignment means engagable upon placement of the bearing insert at the preliminary axial position for retaining the bearing insert at a preliminary circumferential position relative to the shell component, wherein the bearing face is located at an initial selected orientation, the preliminary alignment means enabling holding of the bearing insert at the preliminary axial position for ascertainment of the circumferential position of the bearing insert and the concomitant orientation of the bearing face, and enabling selective withdrawal of the bearing insert from the preliminary axial position for circumferential repositioning of the bearing insert and concomitant reorientation of the bearing face to a selected final orientation corresponding to a predetermined appropriate orientation, final alignment means engagable upon placement of the bearing insert at the fully-seated axial position for aligning the bearing insert at a final circumferential position, wherein the bearing face is at the selected final orientation, relative to the shell component, and locking means engagable in response to placement of the bearing insert at the fully-seated axial position for locking the bearing insert at the fully-seated axial position with a capturing force great enough to capture the bearing insert at the fully-seated axial position within the shell component, with the bearing face at the selected final orientation relative to the implanted position of the shell component, for permanent service in the acetabular cup assembly.

The invention will be understood more fully, while still further objects and advantages will become apparent, in the following detailed description of a preferred embodiment thereof illustrated in the accompanying drawing, in which.

Figure 1:
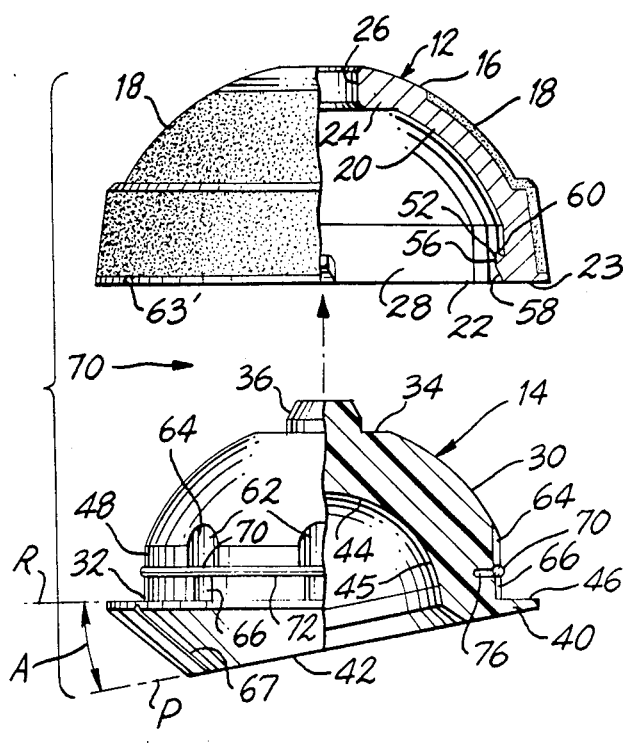
FIG. 1 is an exploded elevational view, partially sectioned, of an acetabular cup assembly constructed in accordance with the invention.

Referring now to the drawing, and especially to FIG. 1 thereof, an acetabular cup assembly constructed in accordance with the invention is illustrated generally at 10. Acetabular cup assembly 10 includes a metallic shell component 12 and a plastic bearing insert 14. Shell component 12 has an outer surface 16, a portion of which is provided with a textured coating 18 enabling the shell component 12 to be fixed in place within an appropriately prepared acetabulum. An inner cavity 20 extends upwardly into the shell component 12, from a lower opening 22 at lower face 23 to a top 24. A hole 26 is located in top 24. Cavity 20 includes a generally cylindrical segment 28 at the lower opening 22. Bearing insert 14 has a domed exterior 30 which is generally complementary to the cavity 20 of shell component 12 and extends from a base 32 to a top 34. A short post 36 projects axially upwardly to engage hole 26 at the top 24 of the shell component 12.

A flange 40 extends circumferentially around the base 32 of bearing insert 14 and projects radially outwardly to provide a transverse bearing face 42 at the base of the bearing insert 14. A bearing socket 44 extends upwardly into bearing insert 14 and provides the spherical bearing surface 45 for a complementary femoral head (not shown). The plane P of bearing face 42 makes a small angle A with radial plane R of the upper surface 46 of flange 40. In the illustrated embodiment, angle A is about 10°. A generally cylindrical portion 48 corresponds to cylindrical segment 28 of the shell component 12.

Acetabular cup assembly 10 is to be implanted in stages; that is, the shell component 12 and the bearing insert 14 are to be assembled interoperatively, so as to enable ascertainment of the appropriate orientation of bearing face 42 within the completed implant, prior to commitment to the completed implant. Such appropriate orientation is determined by provisional trial assessment of the prosthetic hip joint function prior to completing the assembly of bearing insert 14 with the shell component 12, as will be described below. Suffice it to say that shell component 12 is first seated within a prepared acetabulum, and is placed in a fixed position. The bearing insert 14 then is inserted axially into the cavity 20 of shell component 12. In order to provide for the securement of the bearing insert 14 within the shell component 12 with a high degree of retention, while requiring only those levels of assembly forces which are compatible with the surgical environment, acetabular cup assembly 10 is provided with an alignment and securing arrangement enabling ease of assembly along with high retention forces while, at the same time, allowing preliminary positioning, and repositioning as necessary, of the bearing insert 14 within the shell component 12, prior to final seating of the bearing insert 14 in completed assembly with shell component 12, so as to enable ascertainment and adjustment of the orientation of bearing face 42 before commitment to a completed implanted position, in accordance with the aforesaid previous trial assessment.

Figure 2:
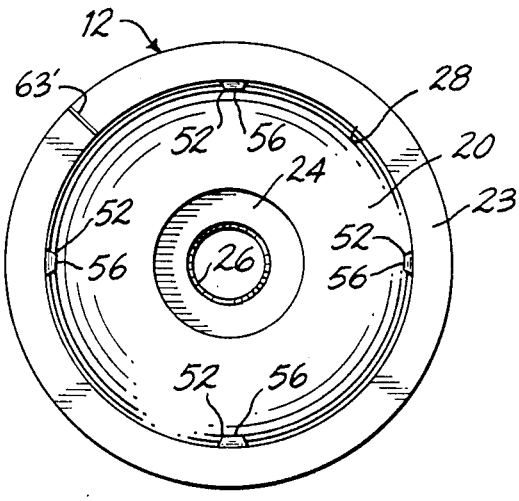
FIG. 2 is a bottom plan view of the shell component of the acetabular cup assembly.
Figure 3:
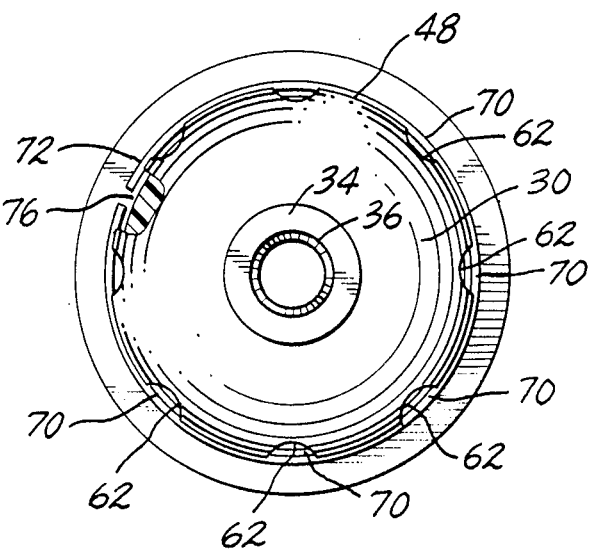
FIG. 3 is a top plan view of the bearing insert component of the acetabular cup assembly.

Turning now to FIGS. 2 and 3, as well as to FIG. 1, the alignment and securing arrangement includes first alignment and securing means having alignment and securing elements shown in the form of barb-like projections 52 integral with shell component 12, spaced circumferentially along cylindrical section 28 of cavity 20, and extending radially inwardly into the cavity 20. In the illustrated embodiment, four projections 52 are shown unitary with shell component 12. Each projection 52 includes an inner radial extremity 56, an inclined surface 58 confronting the lower opening 22 and lower face 23 of the shell component 12 and extending to the extremity 56, and a generally radial shoulder 60 adjacent the extremity 56. The alignment and securing arrangement further includes second alignment and securing means having alignment and securing elements shown in the form of recesses 62 in the bearing insert 14. Recesses 62 extend radially into the bearing insert 14 at cylindrical portion 48. In the illustrated embodiment, recesses 62 are eight in number and are spaced circumferentially such that selected sets of four recesses 62 can be aligned with the four projections 52, enabling the selection of any one of eight different circumferential positions of bearing insert 14 within shell component 12 and, concomitantly, any one of eight different orientations of bearing face 42 relative to shell component 12. Thus, projections 52 are spaced 90° apart from one another, and any set of four recesses 62 spaced 90° apart from one another can be engaged with the projections 52. It will be apparent that the number of and the spacing between the projections 52 and the recesses 62 may be other than that illustrated, enabling a wide variety of selected relative circumferential positions between a mated shell component 12 and bearing insert 14.

Figure 4:
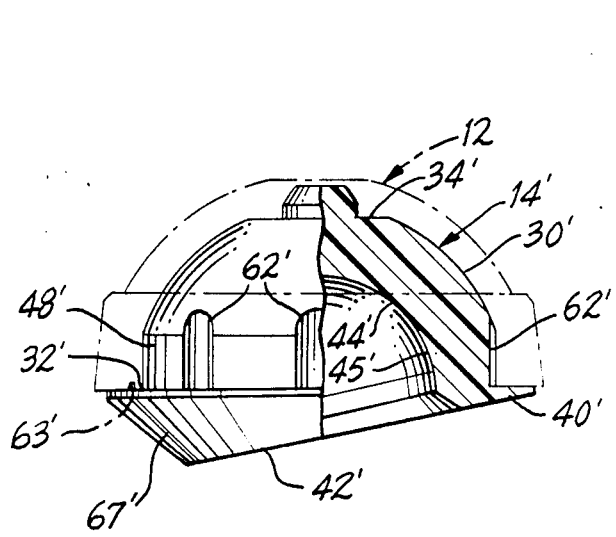
FIG. 4 is an elevational view of a dummy bearing insert.

Preliminary trial assessment of the operation of the acetabular cup assembly is conducted prior to placement of the bearing insert 14 within the shell component 12 in order to determine the proper circumferential position of the bearing insert 14 within the shell component 12 for appropriate orientation of the bearing face 42 relative to the fixed shell component 12. A dummy bearing insert 14', illustrated in FIG. 4, is employed in conducting the preliminary trial assessment. Dummy bearing insert 14' is similar to actual bearing insert 14 and includes a domed exterior 30' which is generally complementary to the cavity 20 of shell component 12 and extends from a base 32' to a top 34'. A flange 40' extends circumferentially around the base 32' and projects radially outwardly to provide a transverse bearing face 42' corresponding to bearing face 42 of bearing insert 14. A bearing socket 44' extends upwardly into dummy bearing insert 14' so that dummy bearing insert 14' provides an analogous spherical bearing surface 45' for the complementary femoral head (not shown). A plurality of recessess 62' extend radially into the dummy bearing insert 14' at cylindrical portion 48' and correspond to recesses 62 in both number and placement.

In conducting the preliminary trial assessment, dummy bearing insert 14' is placed within the shell component 12. The relative dimensions of the recesses 62' and the projections 52 provide sufficient clearance so that the dummy bearing insert 14' is moved readily into a fully-seated position within shell component 12, as illustrated in phantom in FIG. 4. The circumferential position of the dummy bearing insert 14' within the shell component 12 determines the orientation of bearing face 42' relative to the fixed shell component 12. The clearance between projections 52 and recesses 62' enables ready withdrawal of the dummy bearing insert 14' for selective circumferential repositioning of the dummy bearing insert 14' and further trail assessment until the proper circumferential position is determined for appropriate orientation of the bearing face 42' relative to the shell component 12. That position is then marked, using an index line 63 placed in flange 40' as a guide for marking the shell component 12 at a corresponding location 63'. Alternately, the bone surrounding the natural acetabular socket may be marked with an index mark. Once the proper circumferential position is determined and marked, the dummy bearing insert 14' is withdrawn fully from the shell component and the actual bearing insert 14 is inserted into the fixed shell component 12.

Figure 5:
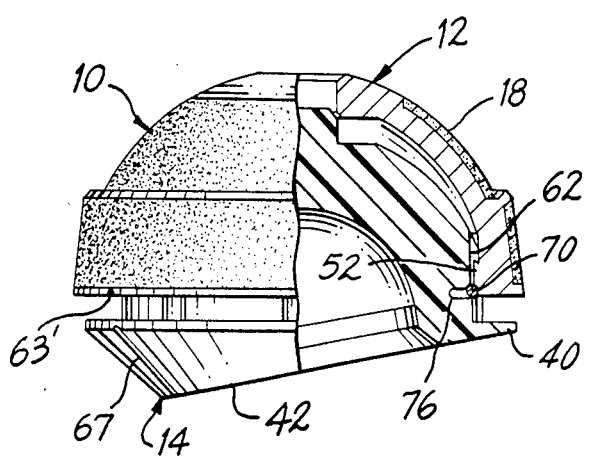
FIG. 5 is an elevational view, partially sectioned, of the component parts in a first stage of assembly.
Figure 6:
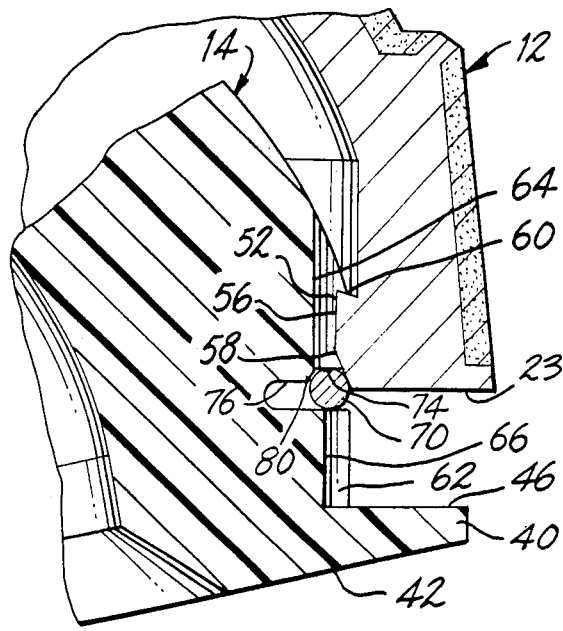
FIG. 6 is an enlarged fragmentary view of a portion of FIG. 4.

The alignment and securing arrangement provides the surgeon with the opportunity for ascertainment and adjustment of the orientation of bearing face 42 so as to match the previously-determined appropriate orientation prior to completing a fully assembled acetabular cup assembly 10. Referring now to FIGS. 5 and 6, as well as to FIGS. 1 through 3, each recess 62 includes an upper guide channel 64 and a lower guide channel 66. The relative dimensions of the upper guide channels 64 and the projections 52 provide clearance between the projections 52 and upper guide channels 64 of the engaged recesses 62 to enable ease of reception of the bearing insert 14 within the shell component 12 and placement of the bearing insert 14 at a preliminary axial position, illustrated in FIGS. 5 and 6. At the preliminary axial position, the bearing insert 14 is not fully seated within the shell component 12, but is retained in a preliminary circumferential position within the shell component 12, allowing axial adjustment and circumferential location of the bearing insert 14 within the shell component 12 in accordance with the previously determined positioning of dummy bearing insert 14'. The ability to move the bearing insert 14 to the preliminary axial position with ease enables the alignment of index line 67 on flange 40 with the mark at location 63'. Thus, any requirement for changes in the orientation of bearing face 42 to match the previously-determined appropriate orientation can be ascertained, prior to committal to a fully assembled acetabular cup. Ample clearance is provided between the projections 52 and the engaged upper guide channels 64 to assure easy withdrawal of the bearing insert 14 from the shell component 12 for selective circumferential repositioning of the bearing insert 14 relative to the shell component 12, as necessary, to attain the most desirable orientation of bearing face 42, as determined previously through the use of dummy bearing insert 14'. The ability to place the bearing insert 14 at the preliminary axial position with ease reduces any tendency for the bearing insert 14 to cock during assembly and facilitates completion of the assembly with the shell component 12, as will now be described.

Figure 7:
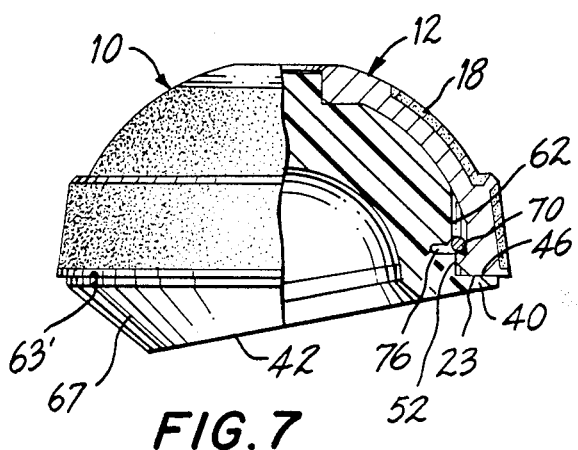
FIG. 7 is an elevational view, partially sectioned, of the component parts in a second stage of assembly.
Figure 8:
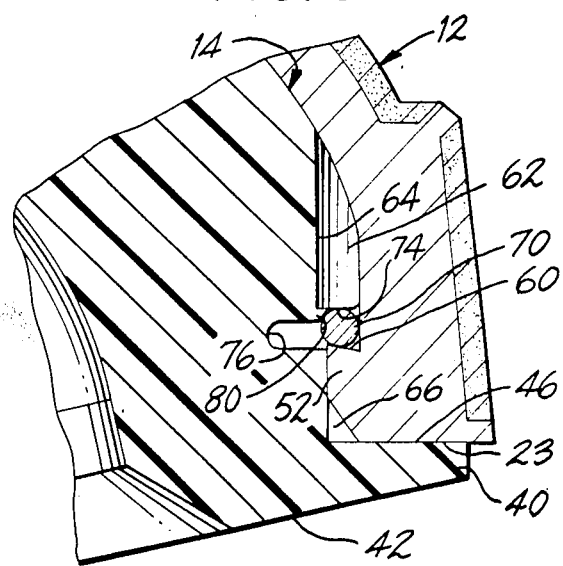
FIG. 8 is an enlarged fragmentary view of a portion of FIG. 6.

Once the appropriate circumferential position of the bearing insert 14 within the shell component 12 has been ascertained, the bearing insert 14 is advanced axially further upwardly into the shell component 12 to a fully-seated axial position, as illustrated in FIGS. 7 and 8. In the fully-seated axial position, the flange 40 of bearing insert 14 confronts the lower face 23 of the shell component 12 and the projections 52 enter the lower guide channels 66 of the recesses 62 engaged by the projections 52. The relative dimensions of the lower guide channels 66 and the projections 52 establish an interference fit between the projections 52 and the recesses 62, thereby tending to secure the bearing insert 14 within the shell component 12 with essentially no circumferential play between the bearing insert 14 and the shell component 12. In order to accomplish permanent capture of the bearing insert 14 within the shell component 12, a locking retention force is attained by locking means in the form of locking bars 70 provided by segments of a split lock ring 72 placed within the mouth 74 of a circumferential groove 76 extending radially into the bearing insert 14, axially between the upper and lower guide channels 64 and 66. Locking bars 70 span the recesses 62 and upon placement of the bearing insert 14 at the fully-seated position, engage the shoulders 60 of projections 52, as seen in FIGS. 7 and 8, to lock the bearing insert 14 in place, captured permanently within the shell component 12.

Figure 9:
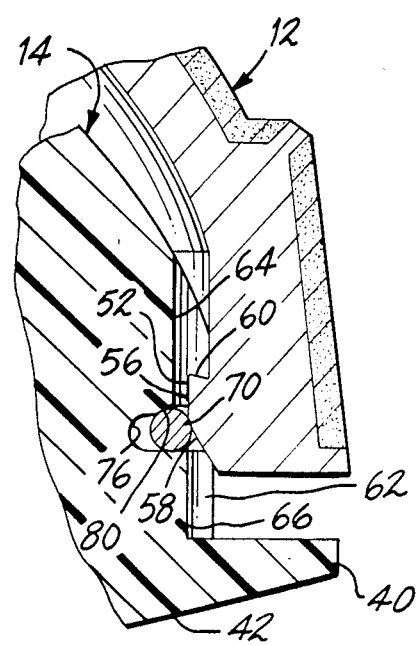
FIG. 9 is an enlarged fragmentary view similar to FIGS. 6 and 8, but with the component parts in an intermediate position.

Preferably, lock ring 72 is constructed of a cobalt alloy which provides the necessary strength and longevity in the environment encountered during the service life of the acetabular cup assembly 10. In addition, the cobalt alloy lock ring 72 functions as a radiographic marker, serving to identify the position of the bearing insert 14 should the bearing insert 14 be inadvertently disassembled from the shell component 12. However, the cobalt alloy lock ring 72 does not possess sufficient elastic properties to first be compressed radially to pass over the projections 52 and then expand radially to engage shoulders 60 for proper retention. In order to provide sufficient radially outward biasing of the locking bars 70, groove 76 includes a constriction 80 adjacent the mouth 74 of the groove 76. As best seen in FIG. 9, as the bearing insert 14 is moved from the preliminary axial position toward the fully-seated axial position, each lock bar 70 will be urged radially inwardly by the inclined surface 58 of projection 52, and into the constriction 80, against the resilient bias of the plastic material at the constriction 80. Once the projection 52 axially passes the locking bar 70, the radially outward biasing force exerted upon the locking bar 70 by the renitence of the plastic material at the constriction 80 will urge the locking bar 70 radially outwardly to engage the shoulder 60, as seen in FIG. 8, and maintain the locking bar 70 in that locking position. Thus, the constriction 80 serves as a biasing means to enable the lock ring 72 to perform its locking function in response to movement of the bearing insert 14 into the fully-seated axial position.

The above-described arrangement enables preliminary positioning of the bearing insert 14 to ascertain the appropriate orientation of the bearing face 42 relative to the fixed shell component 12, and subsequent full seating of the biasing insert 14 within the shell component 12 with only minimal axial assembly force. The required assembly force is readily available to the surgeon, during the implant operation, through the use of an appropriate impactor. Typical assembly forces necessary to effect the capture of a bearing insert 14 within a shell component 12 have been measured at twenty-five to thirty pounds, while the retention force attained by the above-described locking mechanism has been determined to be in excess of one-hundred-fifty pounds.

Thus, the combination of the projections 52 with the recesses 62 provide for the selective circumferential alignment of the bearing insert 14 within the shell component 12, prior to permanent retention, through the provision of larger-dimensioned upper guide channels 64 which receive the projections 52 with sufficient clearance for selective insertion of the bearing insert 14 to the preliminary axial position and withdrawal of the bearing insert 14 for repositioning, while the smaller-dimensioned lower guide channels 66 subsequently receive the projections 52 for secured circumferential alignment of the bearing insert 14, with essentially no circumferential play, upon further movement of the bearing insert 14 axially upwardly beyond the preliminary axial position to the fully-seated position. At the fully-seated position, the projections 52 also serve as axial securing elements by virtue of the lock bars 70 engaging the shoulders 60 to capture the bearing insert 14 within shell component 12. Acetabular cup assembly 10 therefore can be assembled interoperatively, allowing the implant to take place in stages: First, the placement of the shell component 12 in the acetabulum, and then the insertion of the bearing insert 14 into the shell component 12, with ascertainment of the appropriate orientation of the bearing face 42 as a result of preliminary assessment of the operation of the prosthesis, with concomitant adjustments being available during implant and prior to commitment to a completed assembly.

It is to be understood that the above detailed description of a preferred embodiment of the invention is provided by way of example only. Various details of design and construction may be modified without departing from the true spirit and scope of the invention, as set forth in the appended claims.

The embodiments of the invention in which an exclusive property or privilege is claimed are defined as follows:

1. An acetabular cup assembly capable of being implanted in stages so as to enable preliminary ascertainment and adjustment of position during implant and prior to commitment to a completed implanted position, said acetabular cup assembly comprising:
    a shell component having an outer surface for enabling permanent implant of the shell component at an implanted position, an upper top, a lower opening and an inner cavity extending into the shell component upwardly from the lower opening;
    a bearing insert for placement within the cavity of the shell component by movement of the bearing insert in an axial direction into the cavity, the bearing insert being initially movable into a preliminary axial position within the shell component and subsequently movable axially upwardly beyond the preliminary axial position into a fully-seated axial position within the shell component, the bearing insert having a bearing face extending transverse to said axial direction;
    an alignment and securing arrangement for aligning and securing the bearing insert within the shell component, said alignment and securing arrangement including first alignment and securing means carried by the shell component and second alignment and securing means carried by the bearing insert, the first and second alignment and securing means being generally complementary to one another for engagement when the bearing insert is in either of the preliminary and fully-seated axial positions;
    the alignment and securing means including alignment and securing elements, the number and circumferential location of the alignment and securing elements being such that the bearing insert may be placed within the cavity in any selected one of a plurality of circumferential positions relative to the shell component for selective orientation of the bearing face relative to the shell component;
    the alignment and securing elements including preliminary alignment means engagable upon placement of the bearing insert at the preliminary axial position for retaining the bearing insert at a preliminary circumferential position, relative to the shell component, wherein the bearing face is located at an initial selected orientation, the preliminary alignment means enabling holding of the bearing insert at the preliminary axial position for ascertainment of the circumferential position of the bearing insert and the concomitant orientation of the bearing face, and enabling selective withdrawal of the bearing insert from the preliminary axial position for circumferential repositioning of the bearing insert and concomitant reorientation of the bearing face to a selected final orientation corresponding to a predetermined appropriate orientation, final alignment means engagable upon placement of the bearing insert at the fully-seated axial position for aligning the bearing insert at a final circumferential position, wherein the bearing face is at the selected final orientation, relative to the shell component, and locking means engagable in response to placement of the bearing insert at the fully-seated axial position for locking the bearing insert at the fully-seated axial position with a capturing force great enough to capture the bearing insert at the fully-seated axial position within the shell component, with the bearing face at the selected final orientation relative to the implanted position of the shell component, for permanent service in the acetabular cup assembly.

2. The invention of claim 1 wherein at least one of the first and second alignment and securing means includes a plurality of said alignment and securing elements spaced circumferentially from one another, and the other of the first and second alignment and securing means includes at least one further said alignment and securing element complementary with any selected one of said plurality of alignment and securing elements for selective placement of the bearing insert at a corresponding selected circumferential position relative to the shell component, and concomitant orientation of the bearing face relative to the implanted position of the shell component.

3. The invention of claim 2 wherein the plurality of alignment and securing elements include a plurality of radially-extending recesses spaced circumferentially from one another, and said one further alignment and securing element includes a radially-extending projection receivable within any selected one of said recesses.

4. The invention of claim 3 wherein:
each of said recesses includes a first guide channel extending axially along the recess and a second guide channel extending axially along the recess adjacent to and aligned axially with the first guide channel;
the projection is generally complementary to each of said first and second guide channels; and
the relative dimensions of the projection and the first guide channel are such that the projection is received within the first guide channel with sufficient clearance to enable ready selective withdrawal of the bearing insert from the preliminary axial position for circumferential repositioning of the bearing insert in the shell component.

5. The invention of claim 4 wherein the relative dimensions of the projection and the second guide channel are such that the projection is received within the second guide channel in an interference fit to secure the bearing insert circumferentially at the final circumferential position relative to the shell component.

6. The invention of claim 4 wherein the locking means includes:
the projection having a radial extremity, an inclined surface confronting the lower opening of the shell component and extending to the radial extremity, and a radial shoulder adjacent the radial extremity and confronting the upper top of the shell component; and
the plurality of alignment and securing elements having a radially-extending circumferential groove, the groove including a mouth located axially between the first and second guide channels, and a locking bar placed within the mouth of the groove such that upon axial movement of the bearing insert from the preliminary axial position toward the fully-seated axial position the locking bar will be urged in a first direction into the groove, by the inclined surface, to pass over the radial extremity of the projection, and biasing means for biasing the locking bar in a direction opposite to the first direction such that upon placement of the bearing insert at the fully-seated axial position the locking bar will be urged into locking engagement with the radial shoulder of the projection to establish the capturing force.

7. The invention of claim 6 wherein the biasing means includes a constriction in said groove, whereby the renitence of the material bounding the constriction biases the locking bar into said locking engagement.

8. An acetabular cup assembly capable of being implanted in stages so as to enable preliminary ascertainment and adjustment of position during implant and prior to commitment to a completed implanted position, said acetabular cup assembly comprising:
a shell component having an outer surface for enabling permanent implant of the shell component at an implanted position, an upper top, a lower opening and an inner cavity extending into the shell component upwardly from the lower opening;
a bearing insert for placement within the cavity of the shell component by movement of the bearing insert in an axial direction into the cavity, the bearing insert being initially movable into a preliminary axial position within the shell component and subsequently movable axially upwardly beyond the preliminary axial position into a fully-seated axial position within the shell component, the bearing insert having a bearing face extending transverse to said axial direction;
a plurality of projections integral with the shell component and extending radially inwardly into the inner cavity, adjacent the lower opening, the projections being spaced circumferentially from one another;
a plurality of recesses extending radially inwardly into the bearing insert, adjacent the bearing face, the recesses being spaced circumferentially from one another and being generally complementary to the projections;
the circumferential spacing between at least some of the recesses corresponding to the circumferential spacing between the projections such that the bearing insert may be placed within the cavity in any selected one of a plurality of circumferential positions relative to the shell component for selective orientation of the bearing face relative to the shell component;
each recess including a first guide channel extending axially along the recess, and a second guide channel extending axially along the recess adjacent to and aligned axially with the first guide channel, the first guide channel being located above the second guide channel;
the location and relative dimensions of the projections and the first guide channels being such that each projection is received within a corresponding first guide channel, upon placement of the bearing insert in said preliminary axial position, thereby enabling ascertainment of the circumferential position of the bearing insert relative to the shell component when the bearing insert is at the preliminary axial position, and with sufficient clearance to enable ready selective withdrawal of the bearing insert from the preliminary axial position for circumferential repositioning of the bearing insert in the shell component to arrive at a predetermined appropriate final orientation of the bearing face; and
locking means having locking elements located on the shell component and on the bearing insert for operation in response to advancing the bearing insert beyond the preliminary axial position to the fully-seated axial position for capturing the bearing insert in the shell component with the bearing face at the predetermined appropriate final orientation.

9. The invention of claim 8 wherein the relative dimensions of the projections and the second guide channels are such that each projection is received within a corresponding second guide channel, upon placement of the bearing insert in the fully-seated axial position, in an interference fit which secures the bearing insert circumferentially relative to the shell component.

10. The invention of claim 9 wherein the locking means includes:
each projection having a radial extremity, an inclined surface confronting the lower opening of the shell component and extending to the radial extremity, and a radial shoulder adjacent the radial extremity and confronting the upper top of the shell component; and a radially-extending circumferential groove, the groove including a mouth located axially between the first and second guide channels, and a locking bar placed within the mouth of the groove adjacent each projection such that upon axial movement of the bearing insert from the preliminary axial position toward the fully-seated axial position the locking bar will be urged in a first direction into the groove, by the inclined surface, to pass over the radial extremity of the corresponding projection, and biasing means for biasing the locking bar in a direction opposite to the first direction such that upon placement of the bearing insert at the fully-seated axial position the locking bar will be urged into locking engagement with the radial shoulder of the corresponding projection to establish the capturing force.

11. The invention of claim 10 wherein the biasing means includes a constriction in said groove, whereby the renitence of the material bounding the constriction biases the locking bar into said locking engagement.

12. The invention of claim 11 wherein the locking elements include a lock ring located within the circumferential groove, the locking bars comprising segments of the lock ring.

13. The invention of claim 12 wherein the lock ring is constructed of a radiographic material.

14. The invention of claim 13 wherein the radiographic material is a cobalt alloy.

15. The invention of claim 8 wherein the number of projections is four, and the projections are spaced circumferentially equidistant from one another.

16. The invention of claim 15 wherein the number of recesses is eight, and the recesses are spaced circumferentially equidistant from one another.

* * * * *